US00PP35895P3

(12) United States Plant Patent
Lyrene et al.

(10) Patent No.: US PP35,895 P3
(45) Date of Patent: Jul. 2, 2024

(54) BLUEBERRY PLANT NAMED 'FL11-51'

(50) Latin Name: ***Vaccinium corymbosum* L.**
Varietal Denomination: FL11-51

(71) Applicant: Florida Foundation Seed Producers, Inc., Marianna, FL (US)

(72) Inventors: Paul M. Lyrene, Micanopy, FL (US); James W. Olmstead, Aptos, CA (US); Patricio R. Munoz Del Valle, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 18/376,534

(22) Filed: Oct. 4, 2023

(65) Prior Publication Data

US 2024/0130258 P1 Apr. 18, 2024

Related U.S. Application Data

(60) Provisional application No. 63/475,139, filed on Oct. 17, 2022.

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 6/368; A01H 5/08
See application file for complete search history.

(56) References Cited

U.S. PATENT DOCUMENTS

PP12,165 P2 10/2001 Lyrene
PP19,341 P2 10/2008 Lyrene

*Primary Examiner* — Keith O. Robinson
(74) *Attorney, Agent, or Firm* — Koenig IP Works, PLLC; Katherine Koenig

(57) ABSTRACT

A new and distinct southern highbush blueberry (*Vaccinium corymbosum* L.) cultivar named 'FL11-51' distinguished at least by a low to very low chilling requirement, vigorous and healthy growth, semi-bushy growth habit with good evergreen production, high early yield, good field disease resistance, and large fruit that are moderately sweet with high wax cover and exhibit small to medium picking scars.

6 Drawing Sheets

Genus and species: *Vaccinium corymbosum* L.
Cultivar denomination: 'FL11-51'.

BACKGROUND OF THE NEW CULTIVAR

The invention relates to a new and distinct hybrid variety of southern highbush blueberry (*Vaccinium corymbosum* L.) plant 'FL11-51'. 'FL11-51' originated as a seedling that was generated from a cross performed in Gainesville, Florida, during February of 2008 between 'FL07-285' (unpatented), as the female (seed) parent, and 'FL06-10' (unpatented), as the male (pollen) plant. The seedling was planted in a high-density field nursery in May of 2009, and the first fruit were evaluated in April of 2010. 'FL11-51' was first asexually propagated during 2011 by softwood stem cuttings in Gainesville, Florida. After the second year of fruiting in the field, 'FL11-51' was propagated by softwood stem cuttings during the spring of 2011 to establish an experimental 15-plant test plot for a variety test that was conducted during January of 2012 in Waldo, Florida. It was during this variety test that the cultivar name 'FL11-51' was assigned. Based on the growth, yield and fruit quality of this plot, 'FL11-51' was repropagated by softwood stem cuttings and additional experimental test plots ranging from 5 to 45 plants were established for experimental research trials throughout Florida. These plots have been observed during flowering and ripening each year since establishment, and no mutations or off-type plants have been observed.

Plant Breeder's Rights for this cultivar have not been applied for. The new blueberry cultivar 'FL11-51' has not been made publicly available for more than one year prior to the filing of this application.

SUMMARY OF THE INVENTION

The new blueberry cultivar 'FL11-51' has not been observed under all possible environmental conditions. The phenotype of the new cultivar may vary with variations in environment and cultural practices such as temperature, light intensity, fertilization, irrigation, and application of plant growth regulators without any change in genotype.

The new cultivar 'FL11-51' differs from its parents and all other known southern highbush blueberry plants. The following are the most distinguishing characteristics of 'FL11-51' when grown under normal horticultural practices in Florida: (1) a low chilling requirement, particularly for the flower buds; (2) a vigorous, round semi-bushy growth habit; (3) high yield during the months of April and May; and (4) large, firm, sweet berries that exhibit small to medium picking scars and strong waxy cover.

Plants of the new cultivar 'FL11-51' can be readily and unambiguously distinguished from those of its parents at least based upon earliness, higher yield, and quality of fruit. The early fruit yield exhibited by plants of 'FL11-51' is significantly earlier than that of 'FL06-10' (male or pollen parent). Also, the fruit diameter of 'FL11-51' is significantly larger than that of 'FL07-285' (female or seed parent).

Blueberry variety 'Emerald' (U.S. Plant Pat. No. 12,165) is planted throughout the southeastern United States. Plants of 'FL11-51' and 'Emerald' can be readily and unambiguously distinguished at least based upon leaf color, the time at which their fruit is produced, and the fruit shape and cluster tightness. Plants of 'FL11-51' display a more intense green leaf color than 'Emerald'. Further, plants of 'FL11-51' produce their fruit significantly earlier than those of 'Emerald' when no growth regulator is used, and the fruit of 'FL11-51' are rounder and with looser clusters compared to 'Emerald'.

DESCRIPTION OF THE FIGURES

The new blueberry cultivar 'FL11-51' is illustrated in the accompanying photographs, which show the plant's flowers, fruit, leaves, and form. Colors shown are as true as can be reasonably reproduced by photographic procedures and may differ from those cited in the detailed description, which accurately describe the colors of 'FL11-51'.

DETAILED BOTANICAL DESCRIPTION OF THE CULTIVAR

Figure 1:
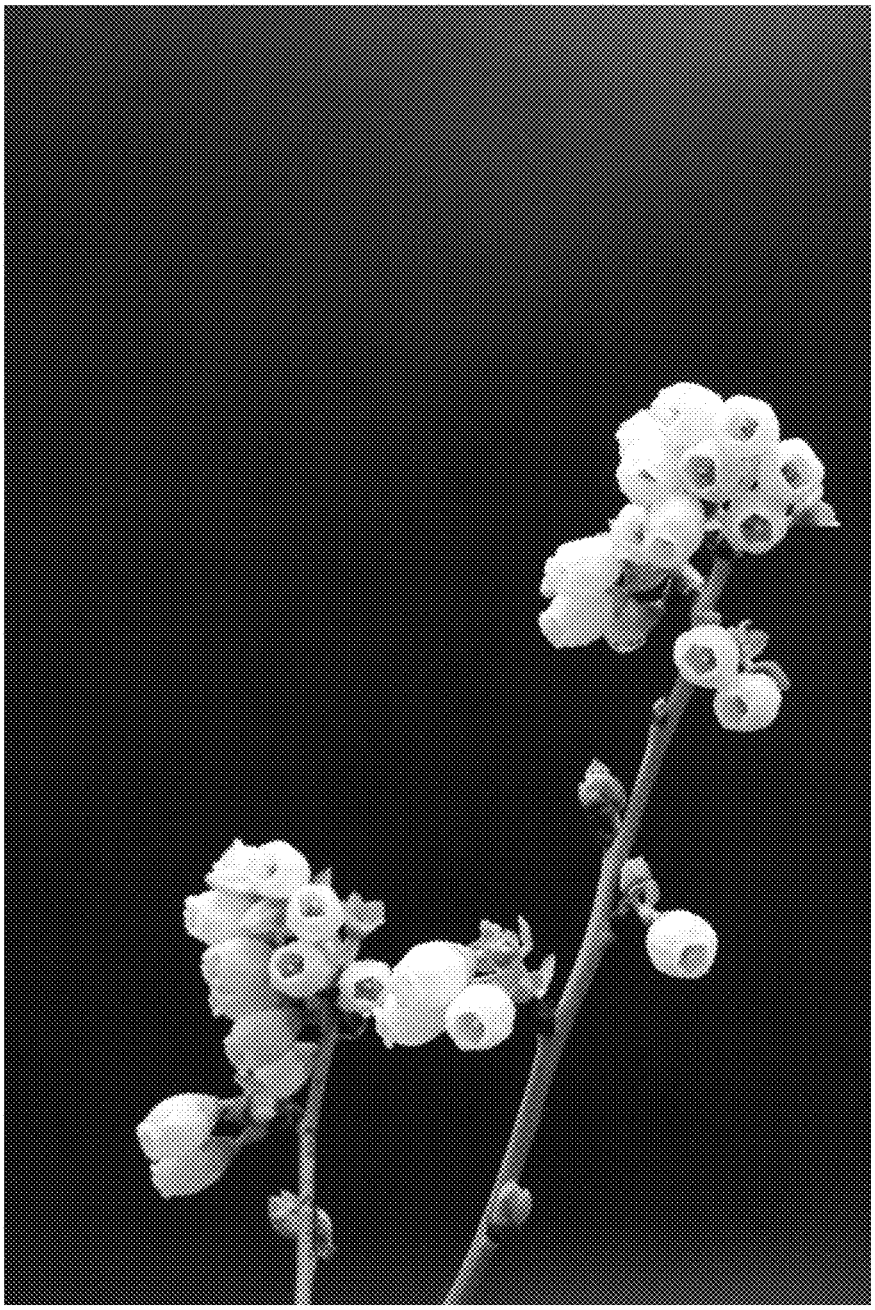
FIG. 1 shows clusters of opening flowers of the new cultivar 'FL11-51'.
Figure 2:
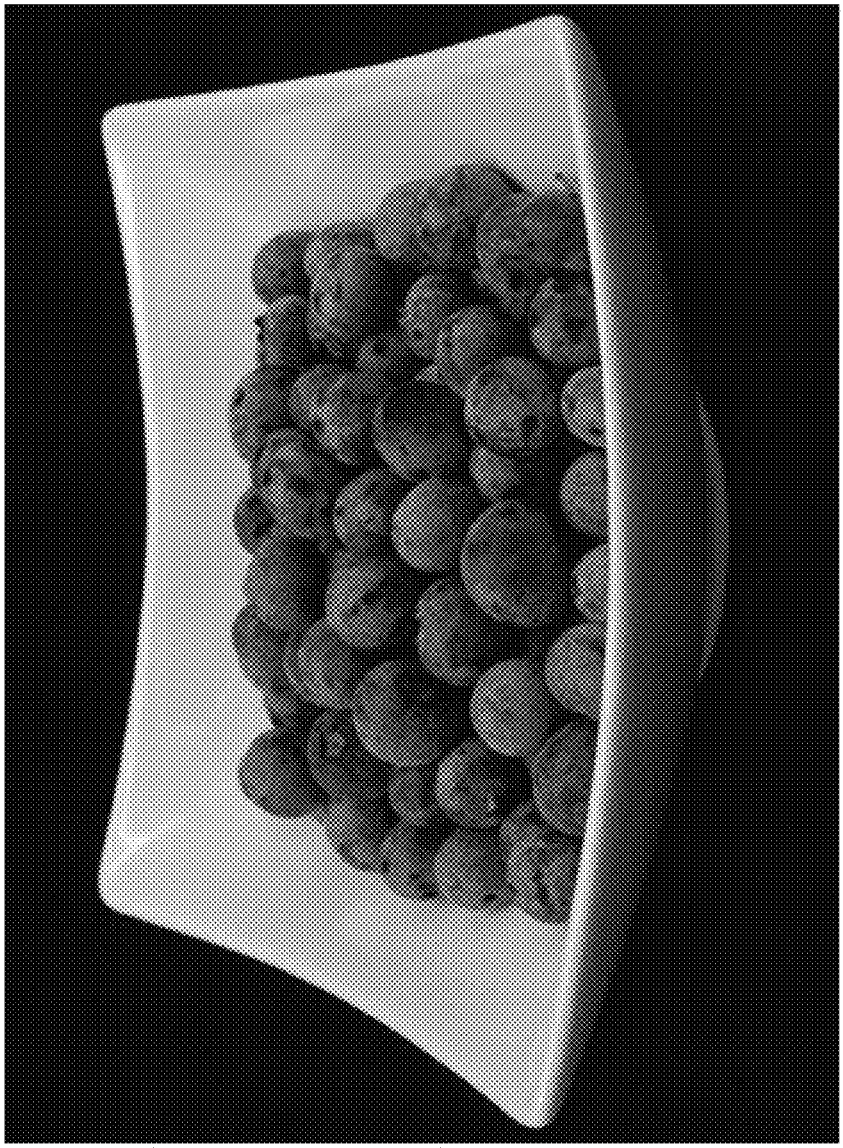
FIG. 2 shows a close-up view of harvested berries of 'FL11-51'.
Figure 3:
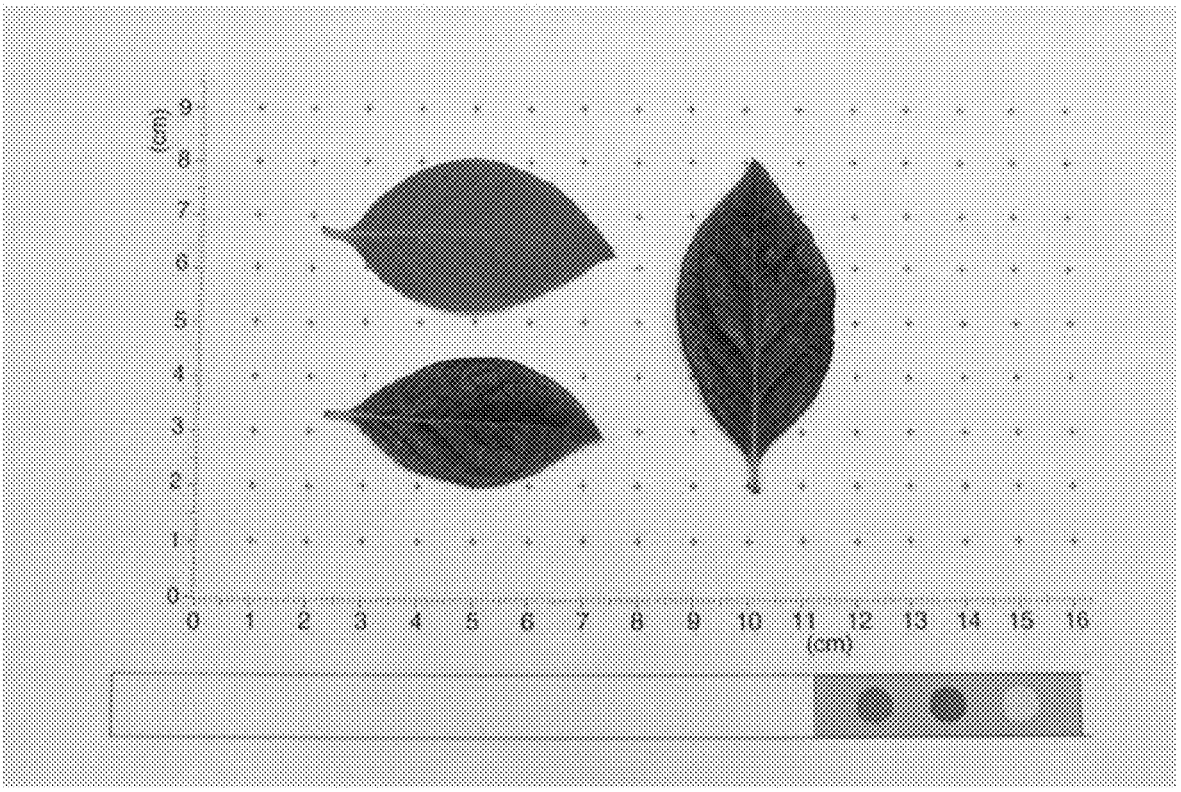
FIG. 3 shows a close-up view of mature leaves of 'FL11-51' with a scale bar.
Figure 4:
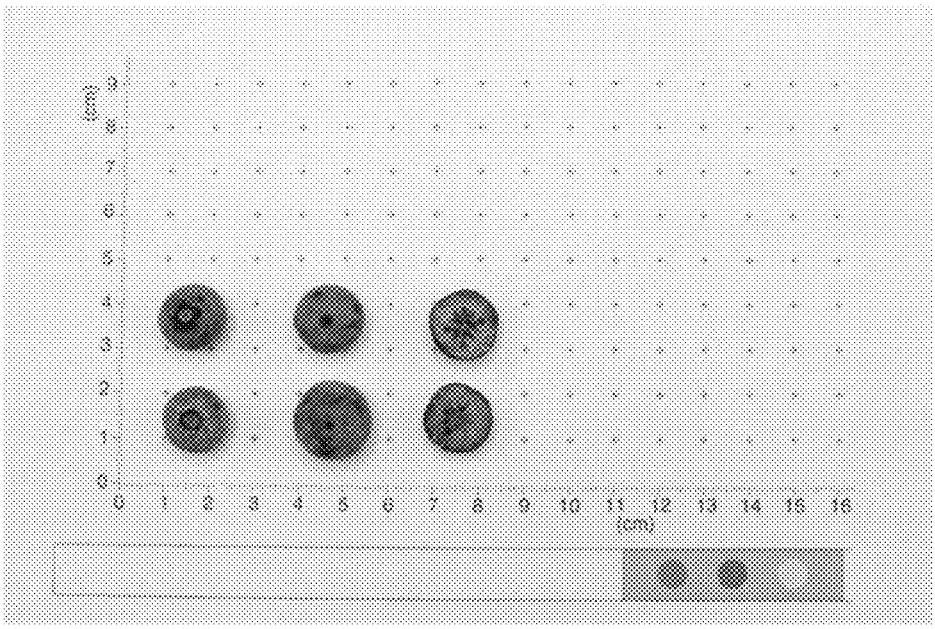
FIG. 4 shows a close-up view of mature fruit of 'FL11-51' with a scale bar.
Figure 5:
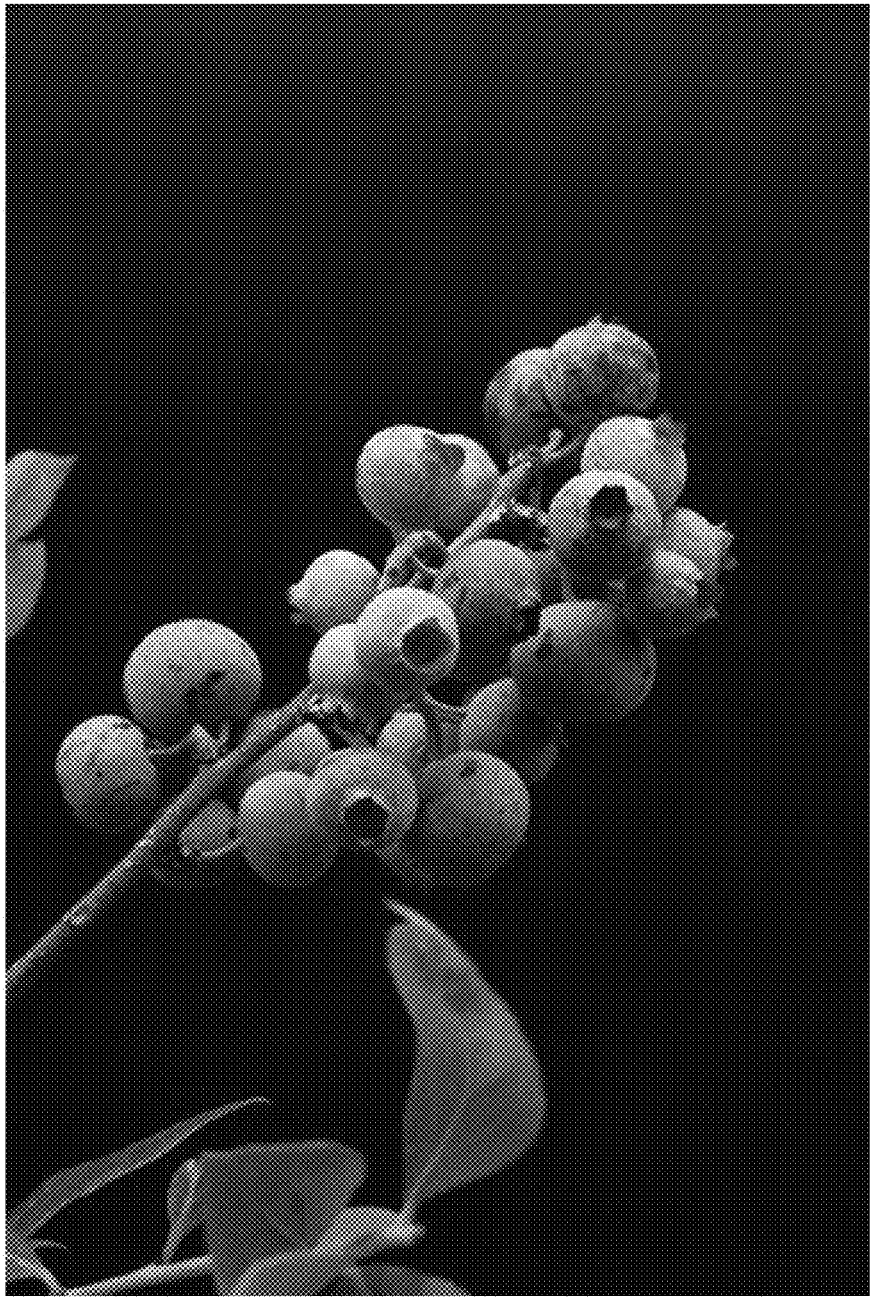
FIG. 5 shows clusters of fruit of 'FL11-51' during the fruit ripening season.
Figure 6:
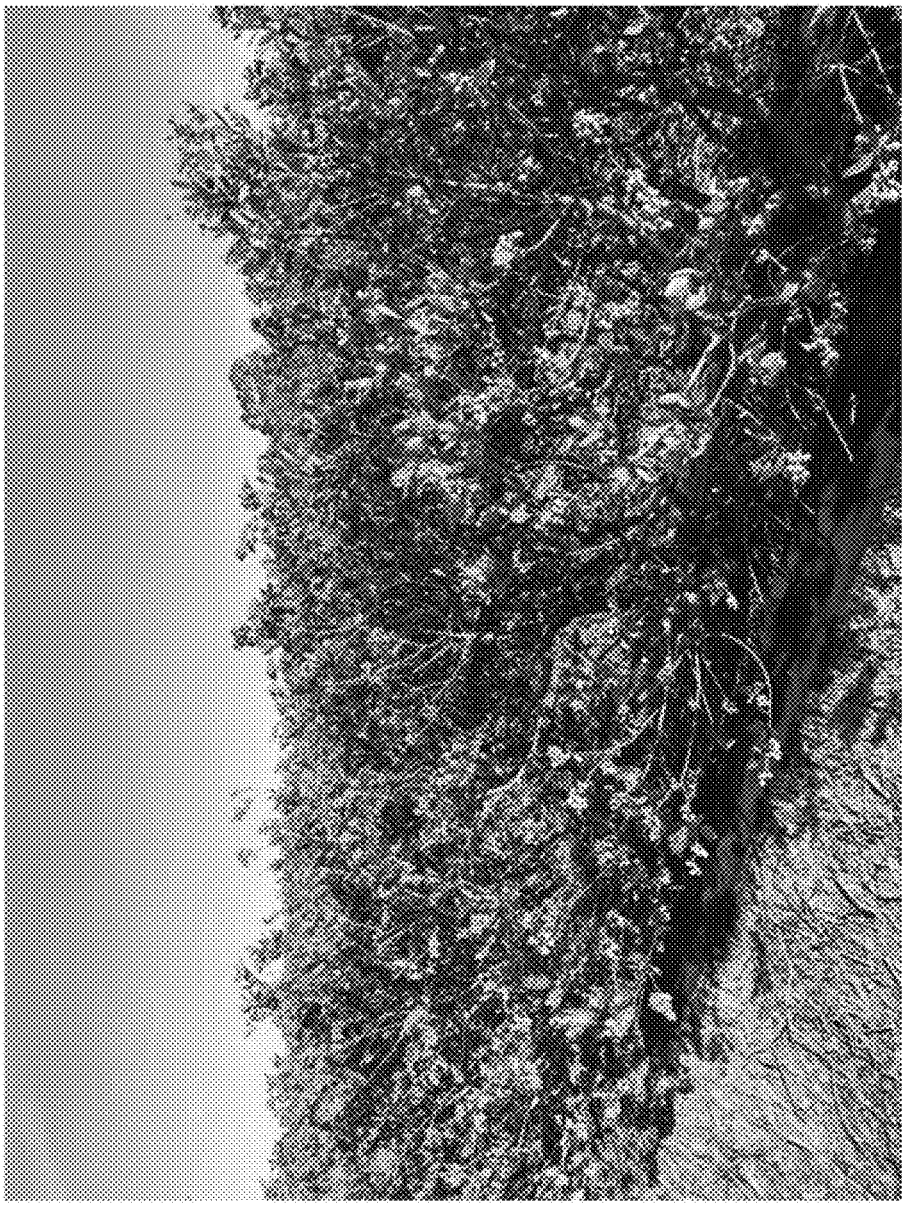
FIG. 6 shows several five-year-old plants of 'FL11-51' on Mar. 13, 2020, with the vigorous, semi-bushy architecture of this new cultivar and its potential productivity.

The following detailed description sets forth distinctive characteristics of the new blueberry cultivar 'FL11-51'. The data that define these characteristics were collected from asexual reproduction plants established in Florida. The plant history was taken on a plot of plants growing in an experimental trial near Citra, Florida (Row 1 East Block). The plants were seven years of age when the data was collected. Certain characteristics may vary with plant age. The new cultivar 'FL11-51' has not been observed under all possible environmental conditions, and the measurements given may vary when grown in different environments. Color descriptions are based on The Royal Horticultural Society (RHS) Colour Chart by The Royal Horticultural Society, London, 6th Edition, (2015). If any RHS color designations below differ from the accompanying photographs, the RHS color designations are accurate.

Botanical description:

Botanical classification:

*Family.*—Ericaceae.

*Botanical name.*—*Vaccinium corymbosum* L.

*Common name.*—Southern Highbush Blueberry.

*Cultivar.*—'FL11-51'.

Parentage:

*Female or seed parent.*—'FL07-285'.

*Male or pollen parent.*—'FL06-10'.

Plant description:

*Plant vigor.*—High.

*Growth habit.*—Semi-bushy, round bush architecture.

*Plant height.*—1.52 m on average for 7-year-old plant.

*Plant diameter.*—2.0 m on average for 7-year-old plant.

*Flower bud density (number) along flowering twigs in January.*—High.

*Twigginess.*—Moderate.

*Tendency toward evergreen growth.*—High, evergreen candidate.

*Productivity.*—In northeast Florida, 'FL11-51' produces 4 kg per season from plants two years old or older when hand harvested.

*Chilling requirement.*—'FL11-51' has been observed producing high yields in years of chill around 50 hours below 7° C.

*Cold hardiness.*—'FL11-51' has been grown in temperate climates with extremely cold winter temperatures. Plants have survived winter freezes of −7° C.with minimal damage.

*Ease of propagation.*—'FL11-51' has only been propagated from softwood stem cuttings, where the rooting percentage is greater than 85% and comparable to other varieties.

Trunk and branches:

*Suckering tendency.*—Medium.

*Surface texture.*—Strong, 12-month-old shoots: Moderately smooth with presence of bark, some bark peeling along the length of the shoot (little to no presence of ridges and bark-like structure). Wood three years old and older: Rough with presence of bark-like structures. Color of new trigs observed in the field: Fan 3 Yellow-Green Group 145 Strong Yellow Green A.

*Color of 3-year-old, rough-textured canes.*—Fan 4 Greyed-Orange Group 165 Moderate Brown A with highlights Fan 4 Greyed-Orange Group 165 Brownish Orange B. Some exposed underlayer from bark peeling has the color Fan 3 Green Group 138 Moderate Yellow Green B.

*Internode length (strong, upright shoots).*—Mean of 17.55 mm.

Foliage description:

*Leaf arrangement.*—Alternate, Fibonacci spiral.

*Length (including petiole, from tip of petiole to end of blade).*—Mean of 5.37 cm.

*Width (at widest point).*—Mean of 2.98 cm.

*Petiole length.*—Mean of 4.07 mm.

*Petiole diameter.*—Mean of 1.43 mm.

*Leaf shape.*—Elliptic with small needle tip on leaf apex. Leaf base shape: Elliptic.

*Leaf venation pattern.*—Reticulate.

*Margin.*—Entire.

*Color.*—Upper surface: Fan 3 Green Group 137 Moderate Olive Green A. Lower surface: Fan 3 Yellow-Green Group 147 Moderate Yellow Green B. Leaf vein color: Fan 3 Yellow-Green Group 147 Moderate Yellow Green D. Leaf petiole color: Fan 3 Yellow-Green Group 147 Moderate Yellow Green D.

*Pubescence.*—Upper surface of leaves: Absent. Lower surface of leaves: Absent. Margins. Absent.

*Timing of vegetative bud burst (early, medium, late).*—Early.

*Relative timing of leafing versus flowering.*—When not treated with hydrogen cyanamide in mid-winter, leafing occurs during flowering.

Inflorescence description:

*Arrangement.*—Flowers are arranged alternately along the branch with leaves.

*Fragrance.*—Very slight floral fragrance.

*Shape.*—Urceolate and cylindrical with some presence of striations.

*Flowering period.*—Mean date of 50% anthesis is between the second and third weeks of January in Waldo, Florida when not treated with hydrogen cyanamide.

*Cluster.*—Medium.

*Number of flowers per cluster.*—Mean of 6.24.

*Pedicel.*—Length at time of anthesis: Mean of 4.27 mm. Color at time of anthesis (side not exposed to sun): Fan 3 Yellow-Green Group 144 Strong Yellow Green C.

*Peduncle.*—Length at time of anthesis: Highly variable, mean of 15.54 mm. Color at time of anthesis (side not exposed to sun): Fan 4 Yellow-Green Group 144 Strong Yellow Green B.

*Calyx.*—Surface texture: Smooth with slight wax. Diameter: Mean of 5.15 mm. Color (outer surface, visible at the time of anthesis without removing the corolla tube): Fan 3 Green Group 133 Light Bluish Green C, with Fan 3 Yellow-Green Group 144 Light Yellow-Green D on tips of calyx lobes.

*Corolla.*—Diameter: Mean of 6.198 mm. Length (from pedicel attachment point to corolla tip excluding the pedicel): Mean of 10.7364 mm. Aperture diameter: Mean of 2.724 mm. Texture: Smooth with slight wax. Color: Fan 4 White Group NN155 Yellowish White A. Anthocyanin coloration in tube: Absent, none detected.

Reproductive organs:

*Style.*—Length (top of ovary to stigma tip): Mean of 8.0748 mm. Color: Fan 3 Yellow-Green Group N144 Strong Yellow-Green D.

*Location of tip of stigma relative to lip of the corolla.*—Stigma tip is approximately 1.07 mm below the corolla lip.

*Anthers.*—Color: Fan 4 Greyed-Orange Group 167 Moderate Orange A. Pollen: High. Pollen germination: Typically, greater 90%. Color: Fan 1 Yellow Group 9 Pale Greenish-Yellow D. Filament length: 6.67 mm. Filament width: 0.92mm.

*Self-fruitfulness.*—Low to medium. Planting in the field configurations that promote cross fertilization with other southern highbush varieties is recommended for all southern highbush blueberry plants grown in Florida.

Fruit:

*Mean date of* 50% *harvest in Citra, Florida.*—Between the $16^{th}$ and $17^{th}$ weeks of the year.

*Diameter of calyx aperture on mature berry.*—Mean of 4.59 mm.

*Size and shape of calyx lobes on mature berry.*—Small to medium, erect to incurving and outcurving with a semi-dry shallow calyx basin.

*Pedicel length on ripe berry.*—Mean of 49.65 mm.

*Detachment force for ripe berries* (*easy, medium, hard*).—Easy.

*Fruit cluster density* (*sparse, medium, dense*).—Medium.

*Number of berries per cluster.*—Mean of 4.08.

*Fruiting type.*—Most prevalent on current season's shoots and on one-year-old shoots to a lesser degree.

*Berry.*—Cluster (tight, medium, loose): Loose. Weight (on well-pruned plants): Mean of 2.13 g (average for 25 berries). Height: Mean of 13.95 mm. Width: Mean of 16.51 mm. Shape: Round, slightly oblate. Surface color of mature berries ripe on the plant: Fan 2 Violet-Blue Group 97 Light Purplish Blue B. Intensity of fruit bloom: Very high. Surface color of ripe berry after polishing: Fan 4 Greyed-Purple Group N186 Dark Purplish Grey A. Immature berry color, with bloom: Fan 3 Yellow-Green Group 144 Strong Yellow Green B. Immature berry color, without bloom: Fan 3 Green Group 138 Moderate Yellow Green C. Flesh color: Fan 3 Yellow-Green Group 145 Light Yellow Green D. Surface wax: Medium and with moderate persistence. Pedicel scar: Small to medium and moderately dry. Mean of 1.54 mm. Firmness: Mean 297.72 g/mm. Flavor: Moderately sweet with low acidity. Intensity of fruit sweetness: Medium. Texture: Good non-mealy, fleshy texture and no stone cells present. Fruit storage quality: Fruit can be stored in good condition for two weeks at 4° C.

*Seeds.*—Color of dried seeds: Fan 4 Greyed-Orange Group 164 Brownish Orange A. Weight of 25 well-developed dried seeds: Mean of 17.8 mg. Length of well-developed dried seeds: Mean of 2.32 mm. Width of well-developed dried seeds: Mean of 1.47 mm.

Use: Produces southern highbush blueberries suitable for hand harvest for the fresh fruit markets.

Resistance to diseases, insects, and mites: The new cultivar 'FL11-51' has vigorous growth and shows good bush survival in the field, with almost no young plants dying soon after planting. Reaction to the various fungal species that cause summer leaf spots (including rust) is lower than those of other southern highbush varieties. Lower levels of target spot (*Crynespora cassiicola*) have been observed, but the plants seem tolerant to it. Fungicide applications may be needed after harvest to reduce foliar diseases and retain leaves into the fall for maximum flower bud set. The new cultivar 'FL11-51' appears to be more tolerant than other southern highbush varieties to spider mites. Susceptibility to typical blueberry insect and mite pathogens such as spotted wing drosophila (*Drosophila suzukii*), blueberry gall midge (*Dasineura oxycoccana*), blueberry chilly thrips (*Scirtothips dorsalis*), blueberry flower thrips (*Frankliniella* spp.), and blueberry bud mite (*Acalitus vaccini*) appear similar to other southern highbush cultivars.

Comparison with known cultivars: The blueberry variety 'Farthing' (U.S. Plant Pat. No. 19,341) is planted throughout the southeastern United States. Plants of the new cultivar 'FL11-51' and 'Farthing' can be readily and unambiguously distinguished at least based upon plant architecture, the time at which their fruit is produced, and the fruit size, presence of color defects, and amount of bloom. Plants of 'FL11-51' display a round bush architecture, while 'Farthing' is more compacted. Plants of 'FL11-51' produce their fruit significantly earlier than those of 'Farthing' when no growth regulator is used. In contrast, the fruit size of 'FL11-51' is larger, with no green back color defects and significant more wax bloom than 'Farthing'.

What is claimed is:

1. A new and distinct cultivar of southern highbush blueberry plant named 'FL11-51', as illustrated and described herein.

* * * * *